(12) United States Patent
Khera et al.

(10) Patent No.: US 10,925,871 B2
(45) Date of Patent: Feb. 23, 2021

(54) PHARMACEUTICAL COMPOSITIONS OF SITAGLIPTIN

(71) Applicant: CADILA HEALTHCARE LIMITED, Gujarat (IN)

(72) Inventors: Brij Khera, Pennington, NJ (US); Muthaiyyan Essakimuthu Kannan, Ahmedabad-Gujarat (IN); Jitendra Rameshchandra Patel, Ahmedabad-Gujarat (IN); Saurin Mukundbhai Amin, Ahmedabad-Gujarat (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 0 days.

(21) Appl. No.: 15/121,514

(22) PCT Filed: Feb. 25, 2015

(86) PCT No.: PCT/IN2015/000104
§ 371 (c)(1),
(2) Date: Aug. 25, 2016

(87) PCT Pub. No.: WO2015/128877
PCT Pub. Date: Sep. 3, 2015

(65) Prior Publication Data
US 2016/0367552 A1 Dec. 22, 2016

(30) Foreign Application Priority Data
Feb. 25, 2014 (IN) ............. 651/MUM/2014

(51) Int. Cl.
| | | |
|---|---|---|
| A61K 31/4985 | (2006.01) | |
| A61K 9/20 | (2006.01) | |
| A61K 47/12 | (2006.01) | |
| A61K 9/16 | (2006.01) | |

(52) U.S. Cl.
CPC .......... *A61K 31/4985* (2013.01); *A61K 9/205* (2013.01); *A61K 9/2013* (2013.01); *A61K 9/2018* (2013.01); *A61K 9/2027* (2013.01); *A61K 9/2054* (2013.01); *A61K 9/2081* (2013.01); *A61K 9/2095* (2013.01); *A61K 47/12* (2013.01); *A61K 9/1676* (2013.01)

(58) Field of Classification Search
None
See application file for complete search history.

(56) References Cited

U.S. PATENT DOCUMENTS

| | | |
|---|---|---|
| 6,699,871 B2 | 3/2004 | Edmondson et al. |
| 7,326,708 B2 | 2/2008 | Cypes et al. |
| 2009/0220609 A1* | 9/2009 | Mooney ............ A61K 9/14 424/489 |
| 2009/0247532 A1 | 10/2009 | Huang et al. |
| 2009/0264436 A1* | 10/2009 | McKelvey ......... A61K 9/1635 514/249 |

FOREIGN PATENT DOCUMENTS

| | | |
|---|---|---|
| WO | 2005/020920 A2 | 3/2005 |
| WO | 2005/030127 A2 | 4/2005 |
| WO | 2005/072530 A1 | 8/2005 |
| WO | 2006/033848 A1 | 3/2006 |
| WO | 2007/035198 A2 | 3/2007 |
| WO | 2008/000418 A2 | 1/2008 |
| WO | 2009/084024 A2 | 7/2009 |
| WO | 2009/085990 A2 | 7/2009 |
| WO | 2009/120746 A2 | 10/2009 |
| WO | 2010/000469 A2 | 1/2010 |
| WO | 2010/012781 A2 | 2/2010 |
| WO | 2010/032264 A2 | 3/2010 |
| WO | 2012/131005 A1 | 10/2012 |

OTHER PUBLICATIONS

Shaon Fitzpatrick, et al.; "The development of a stable, coated pellet formulation of a water-sensitive drug, a case study: Development of a stable core formulation": Pharmaceutical Development and Technology: New York, NY, US.: vol. 11. No. 4. Jan. 1, 2006 (Jan. 1, 2006): pp. 521-528. XP008154256: ISSN: 1083-7450. DOI: 10.1080/10837450600941079: p. 522, right-hand column—p. 523: left-hand column tables p. 526, right-hand column—p. 527: left-hand column.

\* cited by examiner

*Primary Examiner* — Bethany P Barham
*Assistant Examiner* — Barbara S Frazier
(74) *Attorney, Agent, or Firm* — Ladas & Parry LLP

(57) ABSTRACT

The present invention relates to stable oral pharmaceutical compositions of sitagliptin base and processes for the preparation thereof.

7 Claims, No Drawings

PHARMACEUTICAL COMPOSITIONS OF SITAGLIPTIN

RELATED APPLICATION

This application is a national phase entry under 35 USC 371 of International Patent Application No.:PCT/IN2015000104 filed on 25 Feb. 2015, which claims priority from Indian Application No. 651/MUM/2014 filed on 25 Feb. 2014, the disclosures of which are incorporated in their entirety by reference herein.

FIELD OF THE INVENTION

The present invention relates to stable oral pharmaceutical compositions of sitagliptin base and processes for the preparation thereof.

BACKGROUND OF THE INVENTION

Sitagliptin dihydrogen phosphate monohydrate of Formula A, an orally-active inhibitor of the dipeptidyl peptidase-4 (DPP-4) enzyme, chemically designated as 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine phosphate (1:1) monohydrate, is indicated as an adjunct therapy to diet and exercise to improve glycemic control in adults with type 2 diabetes mellitus.

[Formula A]

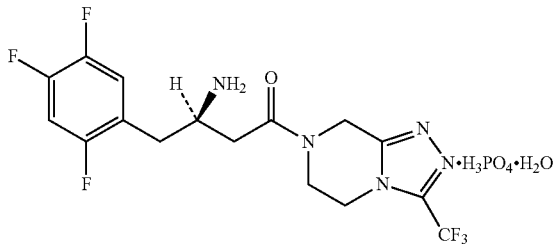

U.S. Pat. No. 6,699,871 (hereinafter "the '871 patent"), in particular Example 7, discloses a process for the preparation of a sitagliptin hydrochloride salt. A list of pharmaceutically acceptable salts is generally disclosed in this patent.

PCT Publication No. WO 2005/072530 discloses a process for the preparation of crystalline salts of sitagliptin with hydrochloric acid, benzene sulfonic acid, p-toluene sulfonic acid, D- and L-tartaric acid and 10-camphorsulfonic acid.

PCT Publication No. WO 2005/030127 discloses a process for the preparation of sitagliptin dihydrogenphosphate anhydrate Form IV. It also discloses a process for the preparation of sitagliptin dihydrogen phosphate anhydrate Form I by heating sitagliptin dihydrogenphosphate anhydrate Form IV at a temperature above 140° C. for about 1 hour.

PCT Publication No. WO 2005/020920 discloses a process for the preparation of crystalline anhydrate Form I, crystalline desolvated anhydrate Form II, crystalline anhydrate Form III, and a crystalline ethanol solvate of sitagliptin dihydrogen phosphate. It also discloses a process for the preparation of a mixture of sitagliptin dihydrogen phosphate anhydrate Form I and anhydrate Form III.

PCT Publication No. WO 2007/035198 discloses a process for the preparation of a dodecylsulfate salt of sitagliptin.

PCT Publication No. WO 2008/000418 discloses a process for the preparation of sitagliptin hydrochloride in amorphous form.

PCT Publication No. WO 2009/120746 discloses processes for the preparation of a crystalline form of sitagliptin phosphate, characterized by a powder XRD pattern with peaks at about 4.7, 13.5, 17.7, 18.3, and 23.7±0.2° 2θ.

PCT Publication No. WO 2006/033848 discloses a process for the preparation of crystalline sitagliptin dihydrogenphosphate monohydrate and amorphous sitagliptin dihydrogenphosphate.

U.S. Publication No. 2009/247532 discloses processes for the preparation of polymorph Form V of sitagliptin phosphate and polymorph Form I of sitagliptin phosphate.

PCT Publication No. WO 2009/084024 discloses a process for the preparation of R-sitagliptin dibenzyl-L-tartrate.

PCT Publication No. WO 2009/085990 discloses a process for the preparation of crystalline anhydrate Form A of sitagliptin dihydrogen phosphate, crystalline sitagliptin sulfate, crystalline sitagliptin hydrobromide, crystalline sitagliptin methane sulfonate, crystalline sitagliptin acetate, crystalline sitagliptin benzoate, crystalline sitagliptin oxalate, crystalline sitagliptin succinate, crystalline sitagliptin mandelate, crystalline sitagliptin fumarate and crystalline sitagliptin lactate.

PCT Publication No. WO 2010/032264 discloses a process for the preparation of crystalline Form 3 of sitagliptin, a crystalline form of dibenzoyl-L-tartaric acid salt of sitagliptin, an amorphous form of sitagliptin and a crystalline form of sitagliptin phosphate.

PCT Publication No. WO 2010/000469 discloses a process for the preparation of sitagliptin hydrochloride Form I, sitagliptin hydrochloride Form II, sitagliptin fumarate Form I, sitagliptin fumarate Form II, sitagliptin maleate, sitagliptin sulfate Form I, sitagliptin sulfate Form II, sitagliptin phosphate, sitagliptin succinate Form I, sitagliptin succinate Form II, sitagliptin succinate Form III, sitagliptin lactate, sitagliptin glycolate, sitagliptin maleate Form I, sitagliptin maleate Form II, crystalline sitagliptin citrate, amorphous sitagliptin citrate, sitagliptin mesylate Form I and sitagliptin mesylate Form II.

PCT Publication No. WO 2010/012781 discloses a process for the preparation of sitagliptin galactarate, sitagliptin hemi-L-maleate, sitagliptin D-gluconate, sitagliptin succinate, sitagliptin hydrobromide, sitagliptin thiocyanate, sitagliptin oxalate, sitagliptin aspartate, sitagliptin ethanedisulfonate, sitagliptin pyroglutamate, sitagliptin glutarate, sitagliptin acetate, sitagliptin hydrochloride amorphous form, sitagliptin citrate amorphous form, sitagliptin hemicitrate amorphous form, sitagliptin glycolate amorphous form and sitagliptin maleate amorphous form.

U.S. Pat. No. 7,326,708 discloses crystalline sitagliptin dihydrogenphosphate monohydrate and a process for its preparation. It also discloses that the crystalline dihydrogenphosphate salt of the present invention exhibits pharmaceutic advantages over the free base and the previously disclosed hydrochloride salt.

The film-coated tablets Januvia® are being marketed by Merck in the USA. The Januvia® tablet contains 32.13, 64.25, or 128.5 mg of sitagliptin phosphate monohydrate, which is equivalent to 25, 50, or 100 mg, respectively, of free base.

In the pharmaceutical industry, there is a constant need to work on identifying different pharmaceutical compositions that positively affect the drug's dissolution profile, bioavailability, bioequivalence, stability, etc., which all play important roles in determining a drug's market acceptance and success.

In the case of sitagliptin too, there is a need for the development of pharmaceutical compositions with improved solubility, stability, excellent storage and handling stabilities, bioavailability, etc.

We have found that stable pharmaceutical compositions can be prepared even by using sitagliptin base as an active pharmaceutical ingredient.

SUMMARY OF THE INVENTION

In one general aspect there is provided a stable pharmaceutical composition comprising sitagliptin and at least one beneficial agent, wherein the composition is a bioequivalent composition to Januvia® and shows similar rate and extent of absorption to those of Januvia®, the currently marketed product of sitagliptin phosphate monohydrate in USA.

In another general aspect there is provided a stable pharmaceutical composition comprising sitagliptin and at least one beneficial agent selected from a complexing agent, a pH modifying agent, a solubilizing compound, a stabilizing compound, a permeability enhancing compound, or a combination thereof.

In another general aspect there is provided a stable pharmaceutical composition comprising sitagliptin and alginic acid as a beneficial agent.

In another general aspect there is provided a stable pharmaceutical composition of sitagliptin wherein a solid dispersion of sitagliptin is prepared.

In another general aspect there is provided a stable pharmaceutical composition comprising sitagliptin and at least one beneficial agent, wherein the sitagliptin is micronized.

In another general aspect there is provided a stable pharmaceutical composition comprising sitagliptin, at least one beneficial agent and one or more pharmaceutically acceptable excipients, wherein said composition retains at least about 90% of the potency of sitagliptin in the pharmaceutical composition after storing the composition at 40° C. and 75% relative humidity at least for three months.

Embodiments of the pharmaceutical composition may include one or more of the following features. For example, the pharmaceutical composition may further include one or more pharmaceutically acceptable excipients. The pharmaceutically acceptable excipients may include one or more diluents, binders, disintegrants, glidants, lubricants, sweeteners/taste masking agents, compression aids, colorants, flavors and the like.

In still another aspect there is provided a stable pharmaceutical composition of sitagliptin, wherein the composition is made up of admixing and/or granulating sitagliptin with at least one beneficial agent and one or more pharmaceutically acceptable excipients and processing the mixture to provide a final dosage form.

In still another aspect there is provided a stable pharmaceutical composition of sitagliptin, wherein the composition is made up of preparing a homogeneous melt by mixing sitagliptin with a suitable binder, cooling the melt, milling and sizing to obtain granules, blending the granules with at least one beneficial agent and one or more pharmaceutically acceptable excipients; and compressing the blend to obtain tablets.

In another general aspect there is provided a stable pharmaceutical composition comprising sitagliptin and at least one beneficial agent, wherein the composition provides an in-vivo plasma profile for sitagliptin comprising a mean of Cmax from about 900 ng/mL to about 1000 ng/ml, a mean of AUC from about 8000 ng*hr/mL to about 9000 ng*hr/mL; and a mean of Tmax at least about 2 hours.

In another general aspect there is provided a method of treating type 2 diabetes mellitus in a patient comprising administering to said subject a stable pharmaceutical composition comprising sitagliptin, at least one beneficial agent and one or more pharmaceutically acceptable excipients.

The details of one or more embodiments of the present invention are set forth in the description below. Other features, objects and advantages of the invention will be apparent from the description.

DETAILED DESCRIPTION OF THE INVENTION

The inventors have surprisingly found that when a beneficial agent as described herein is used in formulating the composition of sitagliptin, the resulting composition demonstrates suitable dissolution profile which is ideal for oral delivery. Moreover, the composition was also found to be physico-chemically stable as well as possessing improved formulation characteristics. The compositions of the invention have potential to exhibit comparable in vivo performance to those of Januvia®, the marketed tablet dosage form of sitagliptin phosphate monohydrate in USA. The composition as per the current invention is a bioequivalent composition, wherein the rate and extent of absorption is similar to those of Januvia®.

We have also surprisingly found that a solid dispersion of sitagliptin exhibits enhanced stability under accelerated conditions, thus providing a viable solid dispersion product that eliminates the problems related to stability and bioavailability.

Sitagliptin used in the invention is in its base form. The sitagliptin base as per the invention may be in an amorphous or in any suitable crystalline form. Sitagliptin used in the preparation of the pharmaceutical composition may be in a micronized form such that it has an average particle size diameter ($D_{50}$) below 25 microns, preferably below 15 microns, more preferably below 10 microns and most preferably below 5 microns. The micronized sitagliptin may have a $D_{90}$ below 100 microns, preferably below 50 microns, more preferably below 35 microns.

The term "beneficial agent" used herein, includes but is not limited to a complexing agent, a solubilizing compound, a pH modifying agent, a stabilizing compound, a permeability enhancing compound, or a combination thereof. These agents are used to increase the solubility of sitagliptin in base form. The use of this beneficial agent also provides storage stability to the final composition.

The term "complexing agent" that is represented by, but not limited to, cyclodextrins, including cyclodextrin derivatives, such as α-cyclodextrins, β-cyclodextrins, γ-cyclodextrins, hydroxypropyl-β-cyclodextrin, and sulfobutyl ethyl β-cyclodextrin. The highly soluble complex of sitagliptin and cyclodextrin is prepared by mixing sitagliptin and cyclodextrin together in the presence of water. The concentration of cyclodextrin is preferably high to facilitate the formation of sitagliptin-enhancer complex. In the case when the complexing agent is hydroxypropyl-β-cyclodextrin, the concentration of the hydroxypropyl-β-cyclodextrin solution used for mixing with sitagliptin is greater than 2%, preferably greater than 20%, and more preferably at least about 40%. The amount of sitagliptin is determined by a desired ratio of hydroxypropyl-β-cyclodextrin to sitagliptin, which is preferably less than 20:1, and more preferably less than 5:1. The mixing time of the complex solution is from about one hour to about 48 hours and preferably from about 5 hours to about 24 hours. The addition of hydroxypropyl-β-cyclodextrin and sitagliptin can be incremental to reduce the viscosity of the complex solution and to achieve better complexation.

The term "pH modifying agent" that is represented by, but not limited to a pharmaceutically acceptable organic or inorganic acid substance. Examples thereof include but are not limited to a carbomer, acid anhydride, alginic acid, a latent acid such as glucono-d-lactone, organic acids that contain one or more acidic groups, preferably compounds containing acidic groups selected from carboxylic and sulfonic acid groups, more preferably those which are solid at ambient temperature, and most preferably those which have two or more acidic groups, mono, di- or polybasic carboxylic acids and mono, di or tri-sulfonic acids such as sorbic acid adipic acid, malonic acid, glutaric acid, maleic acid or fumaric acid. Other examples include water-soluble aryl carboxylic acids containing up to 20 carbon atoms or substituted carboxylic acids, for example hydroxy substituted monocarboxylic acids such as gluconic acid, solid forms of lactic acid, glycolic acid or ascorbic acid; hydroxy substituted dicarboxylic acids such as malic acid, tartaric acid, tartronic acid or mucic acid; tri-carboxylic acids, for example citric acid; or amino acids with an acidic side chain, such as glutamic acid, L-cysteine hydrochloride or aspartic acid. The pH modifying agent may include inorganic acidic substance like concentrated hydrochloric acid (HCl), phosphoric acid, boric acid, sulfuric acid. A pH modifying agent is employed in the embodiments of the present invention to shift the pH within and in the vicinity of the sitagliptin composition to more acidic conditions. The use of solid acids or pharmaceutical acceptable salts thereof as pH modifying agent is particularly convenient for the manufacture of compositions according to the embodiments of the present invention. The pH modifying agent used in the composition may provide the pH from 3 to 8, preferably around 5 to the composition.

The term "solubilizing compound" that is represented by, but not limited to surfactants; hydrocolloids such as cellulose derivatives (e.g. hydroxypropyl methyl cellulose, hydroxypropyl cellulose, hydroxyl methyl cellulose); polymers such as N-vinyl-2-pyrrolidone, polyvinyl pyrrolidone; copolymers such as copolymer of vinylpyrrolidone (VP) and vinylacetate (VA).

Suitable "surfactants" used for preparing a pharmaceutical composition of sitagliptin may include one or more of cationic, anionic, non-ionic, zwitterionic surfactants or mixtures thereof.

Suitable cationic surfactants may include one or more of quaternary ammonium compounds, such as benzalkonium chloride, cetyl trimethyl ammonium bromide and dodecyl dimethyl ammonium bromide, hexadecyl (cetyl) trimethyl-ammonium bromide, dodecyl pyridinium chloride, lauryl dimethyl benzyl ammonium chloride, acyl carnitine hydrochlorides, alkyl pyridinium halides, dodecylamine hydrochloride and the like.

Suitable anionic surfactants may include one or more of salts of aliphatic monoesters of sulfuric acid and soaps, such as potassium laurate; sodium dodecyl sulfate; alkyl polyoxyethylene sulfates; sodium alginates; sodium lauryl sulfate and sodium heptadecyl sulfate; sulfonated aromatic agents such as alkyl benzene sulfonic acids and salts thereof, such as tridecylbenzene sulfonic acid and the sodium and amino salts of dodecylbenzene sulfonic acid; alkyl naphthalene sulfonates, such as sodium butylnaphthalene sulfonate, sulfosuccinates such as sodium dioctyl sulfosuccinate and N-acyl-N-alkyl fatty acid taurates; sulfated polyoxyethylated alcohols; sulfated oils; dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid), a pharmaceutically acceptable salts thereof and the like.

Suitable non-ionic surfactants may include one or more of polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxomers), polaxamines, methylcellulose, hydroxycellulose, hydroxy propyl cellulose, hydroxy propylmethylcellulose, noncrystalline cellulose, polyvinyl alcohol, and polyvinylpyrrolidone. In a preferred form of the invention the nonionic surfactant is a polyoxyethylene and polyoxypropylene copolymer and preferably a block copolymer of propylene glycol and ethylene glycol. Such polymers are sold under the tradename Poloxamer also sometimes referred to as Pluronic.

Suitable zwitterionic surfactants may include one or more of alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms such as cocamidopropyl betaine, sodium cocoamphoacetate, cocamidopropyl hydroxysultaine, and sodium cocamphopropionate and the like.

Suitable "stabilizing compound" which may be employed in the invention include, but is not limited to, various organic and inorganic pharmaceutical excipients. Such excipients include various polymers, low molecular weight oligomers and natural products. Representative examples of useful surface stabilizers include hydroxypropylmethylcelluloses, hydroxypropylcelluloses, polyvinylpyrrolidones, dioctylsulfosuccinate, gelatin, casein, lecithin (phosphatides), dextran, gum acacia, cholesterol, tragacanth, polyoxyethylene alkyl ethers (e.g., macrogol ethers such as cetomacrogol 1000), polyoxyethylene castor oil derivatives, polyethylene glycols (e.g., Carbowax 3550 and 934 (Union Carbide)), polyoxyethylene stearates, carboxymethylcellulose calcium, carboxymethylcellulose sodium, methylcelluloses, hydroxyethylcelluloses, hydroxypropylmethylcellulose phthalate, magnesium aluminium silicate, triethanolamine, polyvinyl alcohols (PVA), PEG-derivatized phospholipids, PEG-derivatized cholesterols, PEG-derivatized cholesterol derivatives, PEG-derivatized vitamin A, PEG-derivatized vitamin E, and the like.

Suitable "permeability enhancing compound", which promotes absorption of the drug from the gastrointestinal tract, is preferably a bile acid or an alkali metal salt thereof selected from the group of cholic acid, chenodeoxycholic acid, taurocholic acid, taurochenodeoxycholic acid, glycocholic acid, glycochenocholic acid, lithocholic acid, taurolithocholic acid, ursodeoxycholic acid, dehydrocholic acid, deoxycholic acid, glycodeoxycholic acid, taurodeoxycholic acid, 3-beta-monohydroxycholic acid, 3-alpha-hydroxy-12-ketocholic acid, 3-beta-hydroxy-12-ketocholic acid, and 12-alpha-3-beta-dihydrocholic acid.

Advantageously, the beneficial agents in the composition of the present invention have been found to enhance the wettability and thus, the speed and extent of release and absorption of sitagliptin from the composition. The amount of this beneficial agent in the pharmaceutical composition ranges from about 0.01% to about 50% w/w of the composition, preferably about 0.1% to about 25%, most preferably about 1% to about 20% by weight of the composition.

The term "bioavailability" refers to an extent to which—and sometimes rate at which—the active moiety (drug or metabolite) enters systemic circulation, thereby gaining access to the site of action.

One of the embodiments of the present invention covers a solid dispersion of sitagliptin and one or more pharmaceutically acceptable carriers. There exists mainly two methods of preparing a "solid dispersion": the "solvent" approach, based on the solubilization of the components (active principle and carriers) in a common solvent, followed by evaporation of the solvent; the "molten" approach which includes melting the components (active principle and carriers) at high temperature and then in cooling the mixture in order to allow solidification.

The pharmaceutically acceptable carrier used in solid dispersion is preferably a polymeric carrier, and more preferably is at least one from the group consisting of gelatins, ovalbumin, soybean proteins, gum arabic, non-sucrose fatty acid esters, starches, modified starches, cellulose, methylcellulose (MC), ethylcellulose (EC), hydroxyethylcellulose (HEC), hydroxypropylcellulose (HPC), hydroxypropylmethylcellulose (HPMC), polycarbophil, polyethylene glycol (PEG), polyethylene oxides, polyoxyalkylene derivatives, polymethacrylates, polyvinyl pyrrolidone (PVP), polyvinyl acetate (PVAc), PVP-vinylacetate-copolymer (PVP-VA), Kollidon® VA 64 (a vinylpyrrolidone-vinyl acetate copolymer), lactose, sorbitol, mannitol, maltitol, saccharose, isomalt, cyclodextrins such as α-cyclodextrins, β-cyclodextrins, γ-cyclodextrins, hydroxylpropyl-cyclodextrins, hydroxypropyl-β-cyclodextrin (HP-β-CD), sodium carboxymethyl cellulose, sodium alginate, xantham gum, locust bean gum, chitosan, cross-linked high amylase starch, cross-linked polyacrylic acid (carbopol), or a mixture thereof. In a preferred embodiment, the polymeric carrier suitable for the preparation of a solid dispersion of sitagliptin is HP-β-CD.

The amount of sitagliptin in the solid dispersion of the present invention ranges from about 0.1% to about 95% by weight relative to the total weight of the solid dispersion. In a preferred embodiment, the amount of sitagliptin ranges from about 1% to about 70%, more preferably from about 10% to about 50% by weight relative to the total weight of the solid dispersion. The amorphous solid dispersion of sitagliptin of the present invention is stable during storage.

Pharmaceutically acceptable excipients for use in the pharmaceutical composition may comprise one or more diluents, binders, disintegrants, glidants, lubricants, sweeteners/taste masking agents, compression aids, colorants and flavors.

Suitable diluents or bulking agents which include, but are not limited to, saccharides, including monosaccharides, disaccharides, polysaccharides and sugar alcohols such as arabinose, lactose, dextrose, sucrose, fructose, maltose, mannitol, erythritol, sorbitol, xylitol, lactitol, and other bulking agents such as powdered cellulose, microcrystalline cellulose, starch, dibasic calcium phosphate, tribasic calcium phosphate, calcium carbonate, dextrose, kaolin, magnesium carbonate, magnesium oxide, purified sugar and derivatives thereof.

Suitable binders, which include, but are not limited to, methyl cellulose, hydroxyethyl cellulose, hydroxypropyl cellulose, hydroxypropyl methylcellulose, carbomers, dextrin, ethyl cellulose, methylcellulose, shellac, zein, gelatin, polymethacrylates, polyvinylpyrrolidone, starch, pregelatinized starch, polyvinyl alcohol, tragacanth, sodium alginate, gums, synthetic resins, silicic acid, hydrophilic polymers and the like.

Suitable disintegrants which include, but are not limited to, croscarmellose sodium, crospovidone, sodium starch glycolate, corn starch, potato starch, maize starch and modified starches like pregelatinized starch, calcium silicates, low-substituted hydroxypropylcellulose and the like.

Suitable lubricants and glidants which include, but are not limited to, talc, metallic stearates such as magnesium stearate, calcium stearate, zinc stearate; colloidal silicon dioxide, finely divided silicon dioxide, stearic acid, hydrogenated vegetable oil, glyceryl palmitostearate, glyceryl monostearate, glyceryl behenate, polyethylene glycols, powdered cellulose, starch, sodium stearyl fumarate, sodium benzoate, mineral oil, magnesium trisilicate, kaolin; and the like. It would be appreciated that a person skilled in the art is cognizant of the fact that lubricant, glidant or anti-tacking agent may be used interchangeably. The lubricant, glidant or anti-tacking agent may be present in an amount ranging from 0.1% to 10% w/w of the composition.

Suitable taste masking agents may include one or more of polymers, sweeteners and flavors. Most preferred polymers include one or more of cellulose acetate, polymethacrylates, hydroxypropylmethylcellulose, hydroxypropyl cellulose, hydroxylethyl cellulose; and the like. Suitable sweeteners that may be used, comprises saccharides such as sucrose, dextrose, glucose, maltose, dextrins, D-tagatose, trehalose, dried invert sugar, fructose, levulose, galactose, corn syrup solids, and the like, alone or in combination. Other examples of sweeteners comprise sodium saccharin; aspartame; sugarless sweeteners including polyhydric alcohols such as sorbitol, mannitol, xylitol, glycerol, hydrogenated starch hydrolysates, maltitol, isomaltitol, erythritol, lactitol and the like, alone or in combination. Suitable flavors that may be used, comprise cinnamon, wintergreen, eucalyptus, spearmint, peppermint, menthol, anise as well as fruit flavors such as apple, pear, peach, strawberry, cherry, apricot, orange, watermelon, banana and the like; bean-derived flavors, such as coffee, cocoa and the like or mixtures thereof.

The pharmaceutical composition of sitagliptin may be developed in the form of tablets, capsules, powders, pellets, granules, microspheres, minitablets or any suitable solid unit forms known to person skilled in the art; mouth dissolving tablets; dispersible tablets; effervescent tablets; trilayer tablets; inlay tablets. The preferred dosage forms are tablets and capsules filled with pellets, granules or minitablets as these are more convenient and easier to administer.

In one embodiment, there is provided a stable pharmaceutical composition of sitagliptin comprising sitagliptin, at least one beneficial agent and one or more pharmaceutically acceptable excipients, wherein said composition retains at least about 90% of the potency of sitagliptin in the pharmaceutical composition after storing the composition at 40° C. and 75% relative humidity for at least three months.

The pharmaceutical composition of sitagliptin may be manufactured by using various granulation techniques known to the person skilled in the art, such as, but not limited to direct compression, wet granulation, dry granulation, hot melt granulation, hot melt extrusion, fluidized bed granulation, extrusion, and solvent evaporation.

The components of the pharmaceutical composition defined hereinbefore can be brought together into a suitable composition for oral administration according to standard practice and procedures well known in the art of pharmaceutical science using conventional formulation and manufacturing techniques.

In an embodiment, sitagliptin composition may be prepared by granulating the admixture of sitagliptin and a beneficial agent optionally with one or more pharmaceutical excipients. The resulting granules may be compressed to form tablets or filled in hard gelatin capsules.

Alternatively, the process of manufacturing the sitagliptin composition may comprise a step of granulating sitagliptin with one or more pharmaceutical excipients followed by complete or partial coating of the resulting granules with a beneficial agent. The coated granules may be compressed to form tablets or filled in hard gelatin capsules.

In another embodiment, a stable sitagliptin composition may be developed in the form of pellets, which may be prepared by coating one or more layers of sitagliptin and a beneficial agent on non-pareil sugar seeds or inert cores. The resulting pellets may be admixed with pharmaceutical excipients and filled into hard gelatin capsules or may be compressed with pharmaceutical excipients to form tablets.

Alternatively, the pellets may be prepared by completely or partially coating particles of sitagliptin by a beneficial agent. The resulting pellets may be admixed with pharmaceutical excipients and filled into hard gelatin capsules or may be compressed with pharmaceutical excipients to form tablets.

The composition may be seal coated. Preferably, the composition is seal coated and finally film coated. The composition can be coated with ready color mix systems (such as opadry color mix systems).

In yet another embodiment, the pharmaceutical composition may involve one or more manufacturing process to obtain a single unitary dosage form i.e., wherein the drug is processed by granulation techniques as discussed above and finally compacted to yield a single dosage form.

In yet another embodiment, the stable pharmaceutical composition may be prepared by a process, wherein the process comprises the steps of:
(a) preparing a homogeneous melt by mixing sitagliptin with a suitable binder;
(b) cooling the melt of step (a), milling and sizing to obtain granules;
(c) blending the granules of step (b) with at least one beneficial agent and one or more pharmaceutically acceptable excipients;
(d) compressing the blend of step (c) to obtain tablets; and
(e) optionally, coating the tablets.

In yet another embodiment, the stable pharmaceutical composition may be prepared by a process, wherein the process comprises the steps of:
(a) mixing sitagliptin, at least one beneficial agent and optionally one or more pharmaceutically acceptable excipients;
(b) granulating the mixture of step (a) with or without a binder solution;
(c) blending granules obtained in step (b) with one or more pharmaceutically acceptable excipients; and
(d) compressing the blended granules into a tablet.

In yet another embodiment, the stable pharmaceutical composition may be prepared by a process, wherein the process comprises the steps of:
(a) preparing solution or dispersion of sitagliptin, at least one beneficial agent and optionally one or more pharmaceutically acceptable excipients;
(b) spraying the solution or dispersion of sitagliptin on inert cores;
(c) blending coated cores obtained in step (b) with one or more pharmaceutically acceptable excipients; and
(d) compressing the blended granules into a tablet.

In yet another embodiment, the stable pharmaceutical composition may be prepared by a process, wherein the process comprises the steps of:
(a) mixing sitagliptin and one or more pharmaceutically acceptable excipients; granulating the mixture with or without a binder solution to obtain the sitagliptin granules and optionally coating the granules;
(b) mixing at least one beneficial agent and one or more pharmaceutically acceptable excipients; granulating the mixture with or without a binder solution to obtain the granules and optionally coating the granules;
(c) blending granules obtained in step (a) and (b) with one or more pharmaceutically acceptable excipients; and
(d) compressing the blended granules into a tablet.

In yet another embodiment, the stable pharmaceutical composition may be prepared by a process, wherein the process comprises the steps of:
(a) taking inert cores of sugar spheres;
(b) spraying solution or dispersion of sitagliptin and one or more pharmaceutically acceptable excipients;
(c) spraying solution or dispersion of at least one beneficial agent and one or more pharmaceutically acceptable excipients; and
(d) compressing the coated cores into a tablet.

In yet another embodiment, the stable pharmaceutical composition may be prepared by a process, wherein the process comprises the steps of:
(a) preparing inert cores of at least one beneficial agent;
(b) seal coating of the cores of acid;
(c) spraying solution or dispersion of sitagliptin and one or more pharmaceutically acceptable excipients;
(d) drying the coated cores; and
(e) compressing the coated cores into a tablet.

The compositions as per the invention are tested for assay, dissolution and impurity profile. The compositions are tested for known and unknown impurities under different conditions. One of the known impurities is Impurity-I which is 3-Trifluoromethyl-5,6,7,8-tetrahydro-[1,2,4]triazolo[4,3-a]pyrazine hydrochloride. According to ICH guideline, the level of single known or unknown impurity should not be more than 0.2% in any pack.

In another embodiment, a stable pharmaceutical composition comprising sitagliptin and at least one beneficial agent, wherein the composition provides a mean of $C_{max}$ from about 900 ng/mL to about 1000 ng/ml, a mean of AUC from about 8000 ng*hr/mL to about 9000 ng*hr/mL and a mean of $T_{max}$ at least about 2 hours.

In still another embodiment, a method of treating type 2 diabetes mellitus in a patient comprising administering to said subject a stable pharmaceutical composition comprising sitagliptin, a beneficial agent and one or more pharmaceutically acceptable excipients.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1

TABLE 1a

| Sr. No. | Ingredient | Quantity (% w/w) |
|---|---|---|
| | Intragranular | |
| 1 | Sitagliptin | 22.58 |
| 2 | Microcrystalline cellulose | 26.26 |
| 3 | Dibasic calcium phosphate anhydrous | 22.58 |
| 4 | Croscarmellose sodium | 1.75 |
| 5 | Citric acid | 5.64 |
| 6 | Magnesium stearate | 0.73 |
| 7 | Sodium stearyl fumarate | 0.73 |
| | Extragranular | |
| 8 | Microcrystalline cellulose | 11.29 |
| 9 | Croscarmellose sodium | 1.17 |
| 10 | Magnesium stearate | 1.69 |
| 11 | Sodium stearyl fumarate | 1.69 |
| 12 | Colloidal silicon dioxide | 0.97 |
| | Coating | |
| 13 | Opadry II | 2.91 |
| | Total | 100.00 |

Procedure:

Sitagliptin, microcrystalline cellulose, dibasic calcium phosphate, croscarmellose sodium and citric acid were mixed. The mixture was lubricated with magnesium stearate and sodium stearyl fumarate. The lubricated mixture was roller compacted and compacts were milled and blended with extragranular ingredients like microcrystalline cellulose and croscarmellose sodium. The blend was lubricated with magnesium stearate, sodium stearyl fumarate, colloidal silicon dioxide and was compressed into tablets. The tablets thus obtained were film-coated with opadry II.

Example 2

TABLE 2

| Sr. No. | Ingredient | Quantity (% w/w) |
|---|---|---|
| | Intragranular | |
| 1 | Sitagliptin | 24.27 |
| 2 | Microcrystalline cellulose | 34.22 |
| 3 | Dibasic calcium phosphate anhydrous | 9.71 |
| 4 | Croscarmellose sodium | 3.88 |
| 5 | Fumaric acid | 6.07 |
| 6 | Povidone | 0.97 |
| 7 | polysorbate | 0.49 |
| | Extragranular | |
| 8 | Microcrystalline cellulose | 12.14 |
| 9 | Croscarmellose sodium | 2.91 |
| 10 | Magnesium stearate | 0.97 |
| 11 | Sodium stearyl fumarate | 0.97 |
| 12 | Colloidal silicon dioxide | 0.49 |
| | Coating | |
| 13 | Opadry II | 2.91 |
| | Total | 100.00 |

Procedure:

Sitagliptin, microcrystalline cellulose, dibasic calcium phosphate, croscarmellose sodium and fumaric were mixed. The mixture was granulated using solution of Povidone and poloxamer in Isopropyl alcohol (IPA). The granules were dried. The granules were milled and blended with extragranular ingredients like microcrystalline cellulose and croscarmellose sodium. The blend was lubricated with magnesium stearate, sodium stearyl fumarate, colloidal silicon dioxide and was compressed into tablets. The tablets thus obtained were film-coated with opadry II.

Example 3

TABLE 3

| Sr. No. | Ingredient | Quantity (% w/w) |
|---|---|---|
| | Intragranular | |
| 1 | Sitagliptin | 24.27 |
| 2 | Microcrystalline cellulose | 34.47 |
| 3 | Croscarmellose sodium | 3.88 |
| 4 | Alginic acid | 16.99 |
| 5 | Povidone | 0.97 |
| 6 | Isopropyl alcohol | q.s. |
| | Extragranular | |
| 7 | Macrocrystalline cellulose | 12.14 |
| 8 | Croscarmellose sodium | 2.91 |
| 9 | Magnesium stearate | 0.97 |
| 10 | Colloidal silicon dioxide | 0.49 |
| | Coating | |
| 11 | Opadry II | 2.91 |
| | Total | 100.00 |

Procedure:

Sitagliptin, microcrystalline cellulose, croscarmellose sodium and alginic acid were mixed. The mixture was granulated using solution of Povidone in Isopropyl alcohol (IPA). The mixture was blended with extragranular ingredients like microcrystalline cellulose and croscarmellose sodium. The blend was lubricated with magnesium stearate, colloidal silicon dioxide and was compressed into tablets. The tablets thus obtained were film-coated with opadry II.

The tablets thus prepared were tested for dissolution, assay and impurity profile. The dissolution was carried out in USP Type-I (basket) apparatus having 900 ml purified water as a dissolution medium at 100 RPM. The results of the tests are shown below in Table 3b.

TABLE 3b

| | |
|---|---|
| Assay | 103.4 |
| Dissolution | 87% drug release (in 30 min) |
| Impurity - I | 0.03 |
| Single unknown impurity (maximum) | 0.17 |
| Total impurity | 0.20 |

Example 4

TABLE 4

| Sr. No. | Ingredient | Quantity (% w/w) |
|---|---|---|
| | Intragranular | |
| 1 | Sitagliptin | 20.71 |
| 2 | Microcrystalline cellulose | 41.83 |
| 3 | Crospovidone | 3.31 |
| 4 | Concentrated Hydrochloric acid (HCl) | 8.28 |
| 5 | Povicione | 0.83 |

TABLE 4-continued

| Sr. No. | Ingredient | Quantity (% w/w) |
|---|---|---|
| 6 | Water | q.s. |
| | Extragranular | |
| 7 | Dibasic calcium phosphate anhydrous | 18.64 |
| 8 | Crospovidone | 2.48 |
| 9 | Magnesium stearate | 0.83 |
| 10 | Colloidal silicon dioxide | 0.41 |
| | Coating | |
| 11 | Opadry II | 2.67 |
| | Total | 100.00 |

Procedure:

A binder solution was prepared by dissolving sitagliptin and povidone in HCl-water mixture. Microcrystalline cellulose and crospovidone were mixed and the mixture was granulated using above prepared binder solution. The granules were dried and mixed with extragranular ingredients like dibasic calcium phosphate anhydrous and crospovidone. The blend was lubricated with magnesium stearate, colloidal silicon dioxide and was compressed into tablets. The tablets thus obtained were film-coated with opadry II.

Example 5

TABLE 5

| Sr. No. | Ingredient | Quantity (% w/w) |
|---|---|---|
| | Intragranular | |
| 1 | Sitagliptin | 24.27 |
| 2 | Microcrystalline cellulose | 41.75 |
| 3 | Dibasic calcium phosphate anhydrous | 9.71 |
| 4 | Croscarmellose sodium | 3.88 |
| 5 | Povidone | 0.97 |
| 6 | Water | q.s. |
| | Extragranular | |
| 7 | Microcrystalline cellulose | 7.28 |
| 8 | Maleic acid | 4.85 |
| 9 | Crospovidone | 2.91 |
| 10 | Magnesium stearate | 0.97 |
| 11 | Colloidal silicon dioxide | 0.49 |
| | Coating | |
| 12 | Opadry II | 2.91 |
| | Total | 100.00 |

Procedure:

Sitagliptin, microcrystalline cellulose, dibasic calcium phosphate anhydrous and croscarmellose sodium were mixed. The mixture was granulated using solution of povidone in water. The mixture was blended with extragranular ingredients like microcrystalline cellulose, maleic acid and crospovidone. The blend was lubricated with magnesium stearate, colloidal silicon dioxide and was compressed into tablets. The tablets thus obtained were film-coated with opadry II.

Example 6

TABLE 6a

| Sr. No. | Ingredient | Quantity (% w/w) |
|---|---|---|
| | Intragranular | |
| 1 | Sitagliptin | 24.27 |
| 2 | Microcrystalline cellulose | 38.11 |
| 3 | Dibasic calcium phosphate anhydrous | 9.71 |
| 4 | Croscarmellose sodium | 3.88 |
| 5 | Povidone | 0.97 |
| 6 | Isopropyl alcohol (IPA) | q.s. |
| | Extragranular | |
| 7 | Microcrystalline cellulose | 12.14 |
| 8 | L-cysteine hydrochloride | 3.64 |
| 9 | Crospovidone | 2.91 |
| 10 | Magnesium stearate | 0.97 |
| 11 | Colloidal silicon dioxide | 0.49 |
| | Coating | |
| 12 | Opadry II | 2.91 |
| | Total | 100.00 |

Procedure:

Sitagliptin, microcrystalline cellulose, dibasic calcium phosphate anhydrous and croscarmellose sodium were mixed. The mixture was granulated using solution of povidone in IPA. The mixture was blended with extragranular ingredients like microcrystalline cellulose, L-cysteine hydrochloride and crospovidone. The blend was lubricated with magnesium stearate, colloidal silicon dioxide and was compressed into tablets. The tablets thus obtained were film-coated with opadry II.

The tablets thus prepared were tested for dissolution, assay and impurity profile. The dissolution was carried out in USP Type-I (basket) apparatus having 900 ml purified water as a dissolution medium at 100 RPM. The results of the tests are shown below in Table 6b.

TABLE 6b

| Assay | 100.1 |
|---|---|
| Dissolution | 89% drug release (in 30 min) |
| Impurity - I | 0.08 |
| Single unknown impurity (maximum) | 0.12 |
| Total impurity | 0.58 |

While the invention has been described in terms of its specific embodiments, certain modifications and equivalents will be apparent to those skilled in the art and are intended to be included within the scope of the invention.

The invention claimed is:

1. A stable pharmaceutical composition comprising sitagliptin base and at least one beneficial agent in an amount of about 1% to about 20% by weight of the composition, wherein the beneficial agent is a pH modifying agent which provides pH from about 3 to about 8 to the composition; wherein the pH modifying agent is selected from the group consisting of gluconic acid, lactic acid, glycolic acid, ascorbic acid, malic acid, tartaric acid, tartronic acid and mucic acid; and wherein the composition contains less than 0.2% by weight of 3-Trifluoromethyl-5,6,7,8-tetrahydro-[1,2,4]triazolo[4,3-a]pyrazine hydrochloride (impurity-I) wherein the composition is prepared by a process comprising the steps of:

(a) mixing the sitagliptin base and one or more pharmaceutically acceptable excipients; granulating the mixture with or without a binder solution to obtain sitagliptin granules and optionally coating the granules;

(b) mixing at least one beneficial agent and one or more pharmaceutically acceptable excipients; granulating the mixture with or without a binder solution to obtain granules and optionally coating the granules;

(c) blending the granules obtained in step (a) and (b) with one or more pharmaceutically acceptable excipients; and (d) compressing the blended granules into a tablet.

2. The stable pharmaceutical composition according to claim 1, wherein the sitagliptin is in an amorphous form.

3. The stable pharmaceutical composition according to claim 1, wherein the sitagliptin is in a crystalline form.

4. The stable pharmaceutical composition according to claim 1, wherein the sitagliptin has an average particle size diameter below 25 microns.

5. The stable pharmaceutical composition according to claim 1, wherein the composition further comprises one or more pharmaceutically acceptable excipients comprising diluents, binders, disintegrants, glidants, lubricants, sweeteners/taste masking agents, compression aids, colorants, flavors or the combinations thereof.

6. The stable pharmaceutical composition according to claim 1, wherein the composition is in the form of a solid dispersion.

7. The stable pharmaceutical composition according to claim 1, wherein the beneficial agent is malic acid.

* * * * *